(12) United States Patent
Both et al.

(10) Patent No.: US 7,365,235 B2
(45) Date of Patent: Apr. 29, 2008

(54) PROCESSES FOR PRODUCING BRANCHED COMPOUNDS VIA CONDENSATION AND HYDROGENATION

(75) Inventors: Sabine Both, Duesseldorf (DE); Albrecht Schwerin, Duesseldorf (DE); Erich Reuter, Duesseldorf (DE); Georg Fieg, Mettmann (DE); Juergen Falkowski, Monheim (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 749 days.

(21) Appl. No.: 10/380,929

(22) PCT Filed: Sep. 11, 2001

(86) PCT No.: PCT/EP01/10476

§ 371 (c)(1),
(2), (4) Date: Mar. 18, 2003

(87) PCT Pub. No.: WO02/24621

PCT Pub. Date: Mar. 28, 2002

(65) Prior Publication Data

US 2003/0181769 A1   Sep. 25, 2003

(30) Foreign Application Priority Data

Sep. 20, 2000   (DE) ................ 100 46 434

(51) Int. Cl.
*C07C 29/141*   (2006.01)
*C07C 29/14*    (2006.01)
*C07C 29/136*   (2006.01)

(52) U.S. Cl. ............ 568/881; 568/834; 568/832; 568/822; 568/876; 568/880

(58) Field of Classification Search ........... 568/834, 568/832, 822, 876, 878, 880, 881
See application file for complete search history.

(56) References Cited

U.S. PATENT DOCUMENTS

| 2,088,015 A | 7/1937 | Wickert |
| 2,088,016 A | 7/1937 | Wickert |
| 2,088,018 A | 7/1937 | Wickert et al. |
| 2,921,089 A | 1/1960 | Hagemeyer, Jr. et al. |
| 2,982,784 A | 6/1961 | Reck et al. |
| 4,457,944 A | 7/1984 | Conrad et al. |
| 6,288,288 B1 * | 9/2001 | Springer ............ 568/881 |

FOREIGN PATENT DOCUMENTS

| DE | 31 33 078 A1 | 3/1983 |
| GB | 731917 A | 6/1955 |

OTHER PUBLICATIONS

H. Machemer, "Über die Guerbetsche Reaktion und ihre technische Bedeutung", Angew, Chem., vol. 64, No. 8, (1952), pp. 213-220.

\* cited by examiner

*Primary Examiner*—Elvis O. Price
(74) *Attorney, Agent, or Firm*—John F. Daniels; Jane E. Keene

(57) ABSTRACT

Processes for producing branched compounds are described wherein a carbonyl compound is condensed in the presence of a catalyst selected from the group consisting of acids and bases, to form an α,β-unsaturated condensation product; and the α,β-unsaturated condensation product is hydrogenated.

11 Claims, No Drawings

PROCESSES FOR PRODUCING BRANCHED COMPOUNDS VIA CONDENSATION AND HYDROGENATION

BACKGROUND OF THE INVENTION

Guerbet alcohols are primary alcohols branched in the 2-position which are obtained by condensation of linear fatty alcohols. The products are mainly used as oil components for the production of cosmetic emulsions. They are generally produced from fatty alcohols which, initially, self-condense under the effect of strong bases and heavy metal compounds, for example copper or zinc oxide. It is assumed that, under the reaction conditions, the alcohol is first dehydrogenated to the aldehyde which enters into an aldol condensation with itself, after which the condensation product is hydrogenated to the alcohol. A corresponding overview can be found, for example, in Angew. Chem. 64, 212 (1952). Dialkyl cyclohexanes are similarly produced by double condensation of fatty alcohols with cyclohexanol in the presence of heavy metals.

However, a disadvantage is that, after the reaction, the heavy metal catalysts have to be removed in order to meet legal requirements and to ensure that they do not cause any irritation in the subsequent application. The heavy metal catalysts are generally removed by washing and subsequent distillation which involves considerable product losses. Another disadvantage is that the reaction times are very long and the selectivities are unsatisfactory.

BRIEF SUMMARY OF THE INVENTION

The present invention relates, in general, to cosmetic oil components and, more particularly, to an improved process for the production of, for example, Guerbet alcohols and dialkyl cyclohexanes which does not require heavy metal catalysts for the condensation reaction and which combines improved selectivity with a higher reaction rate.

It has surprisingly been found that branched alcohols or branched hydrocarbons can be obtained by the process according to the invention without the use of heavy metal catalysts in the condensation reaction, both improved selectivities and higher reaction rates being obtained.

DETAILED DESCRIPTION OF THE INVENTION

Carbonyl Compounds

Suitable carbonyl compounds are, above all aldehydes, ketones and mixtures thereof. Suitable aldehydes are, for example, fatty aldehydes which preferably correspond to formula (I):

$$R^1CHO \quad (I)$$

in wich $R^1$ is a linear or branched alkyl group containing 6 to 12 and more particularly 8 to 10 carbon atoms. Typical examples are hexanal, octanal, 2-ethylhexanal, decanal, dodecanal and mixture thereof. Also suitable are fatty ketones, preferably those corresponding to formula(II):

$$R^2COR^3 \quad (II)$$

in which $R^2$ and $R^3$ independently of one another represent linear or branched $C_{6-12}$ alkyl groups. Typical examples are dihexyl ketone, dioctyl ketone, di-2-ethylhexyl ketone, didecyl ketone or didocel ketone. Cyclic ketones, preferably cyclohexanone, may also be used.

Condensation

The condensation reaction may be carried out in known manner, i.e. the carbonyl compounds are initially introduced into the reactor together with the acids or bases and then heated to temperatures of 20 to 250° C. and preferably to temperatures of 200 to 240° C. The reaction may be carried out in the absence of pressure or under pressures of up to 30 bar and preferably up to 5 bar. Suitable catalysts are, in particular, alkali metal bases such as, for example, alkali metal hydroxides or alkali metal carbonates. The catalysts may be used in quantities of 1 to 10 mol-% and are preferably used in quantities of 3 to 5 mol-%, based on the carbonyl compounds. In order to displace the reaction equilibrium onto the product side, it is always advisable continuously to distil off the water of condensation.

Hydrogenation

The hydrogenation of the unsaturated aldehydes or ketones formed as the intermediate product may be carried out using typical hydrogenation catalysts, preferably based on nickel, copper and/or zinc. The hydrogenation is normally carried out at temperatures of 20 to 350° C. and preferably at temperatures of 50 to 250° C. and under pressures of 1 to 300 bar and preferably under pressures of 20 to 250 bar. The reaction products may then be purified by distillation.

EXAMPLES

Example 1

In a stirred reactor consisting of a flask, heating mushroom, water separator, reflux condenser and nitrogen inlet, 1 g (0.015 mol) of potassium hydroxide was added to 500 g (3.2 mol) of decanal (99% by weight) at 20° C., followed by heating to 210° C. The water formed during the reaction was continuously distilled off. After 3 hours, the reaction was terminated, the reaction mixture was cooled to 20° C. and the potassium hydroxide precipitated was filtered off. The resulting clear liquid contained 90% by weight of α,β-unsaturated aldehyde, 4% by weight trimers, 2% by weight esters and 4% by weight unreacted starting aldehyde. The reaction mixture was transferred to an autoclave and hydrogenated for 3 hours at 230° C./250 bar in the presence of a nickel catalyst until there was no further uptake of hydrogen. 90% by weight of the hydrogenation product consisted of 2-octyl dodecanol, 6% by weight of decanol and 4% by weight of trimers. After distillation, the 2-octyl dodecanol was obtained in a purity of 95.7% by weight.

Example 2

As in Example 1, 500 g (3.9 mol) of octanal were condensed in the presence of 1.2 g (0.02 mol) of potassium hydroxide. The resulting product contained 88% by weight of α,β-unsaturated aldehyde, 6% by weight of trimers, 2% by weight of waters and 4% by weight of unreacted octanal. After hydrogenation, a mixture of 88% by weight of 2-hexyl decanol, 6% by weight of octanol and 6% by weight of trimers was obtained. After distillation, the 2-hexyl decanol was obtained in a purity of 93.6% by weight.

Example 3

As in Example 1, 650 g (5.0 mol) of 2-ethyl hexanal and 245 g (2.5 mol) of cyclohexanone were condensed in the presence of 40 g of 45% by weight aqueous potassium hydroxide solution. After 2 hours, the reaction temperature of 240° C. was reached, the end point being indicated by the end of the separation of water. The product was washed with hot water until neutral and dried with sodium sulfate. According to GC analysis, a mixture of 85.4% by weight of disubstituted product, 8.2% by weight of monosubstituted product, 1.3% by weight of 2-ethyl hexanal, 0.3% by weight of cyclohexanone and 4.8% by weight of polymers was present. 500 g of the mixture were hydrogenated for 14 hours at 245° C./20 bar in the presence of 14 g of a nickel catalyst until there was no further uptake of hydrogen. Wet-chemical analysis of the product revealed an acid value of <0.1, an iodine value of 0.4 and a hydroxyl value of 1. GC analysis showed the composition to be 85.4% by weight 2,6-di-(2-ethylhexyl)-cyclohexane, 8.2% by weight 2-(2-ethylhexyl)-cyclohexane, 1.3% by weight 2-ethyl hexane, 0.3% by weight cyclohexane and 4.8% by weight oligomers. The unreacted starting materials were removed by distillation.

What is claimed is:

1. A process for producing branched compounds, comprising the steps of:
   (a) condensing at a temperature from 210° C. to 250° C. a carbonyl compound comprising an aldehyde of the general formula (I):

wherein $R^1$ represents an alkyl group having from 6 to 12 carbons atoms, and/or a ketone of the general formula (II):

wherein $R^2$ and $R^3$ each independently represent an alkyl group having from 6 to 12 carbon atoms, in the presence of an alkali metal base catalyst to form an α,β-unsaturated condensation product; and
   (b) hydrogenating the α,β-unsaturated condensation product.

2. The process according to claim 1, wherein the alkali metal base is selected from the group consisting of alkali metal hydroxides and alkali metal carbonates.

3. The process according to claim 2, wherein the alkali metal base is an alkali metal hydroxide.

4. The process according to claim 2, wherein the alkali metal base is an alkali metal carbonate.

5. The process according to claim 1, wherein the carbonyl compound comprises a cyclic ketone.

6. The process according to claim 1, wherein the hydrogenation is carried out at temperature of from 20 to 350° C.

7. The process according to claim 1, wherein the hydrogenation is carried out in the presence of a catalyst selected from the group consisting of nickel, copper and zinc compounds.

8. The process according to claim 6, wherein the hydrogenation is carried out in the presence of a catalyst selected from the group consisting of nickel, copper and zinc compounds.

9. The process according to claim 1, wherein the hydrogenation is carried out at a pressure of from 1 to 300 bar.

10. The process according to claim 1, further comprising distilling the hydrogenated condensation product.

11. The process according to claim 1, wherein the condensation is carried out in a heavy metal-free reaction medium.

* * * * *